United States Patent [19]

Kossovsky et al.

[11] Patent Number: 5,334,394

[45] Date of Patent: * Aug. 2, 1994

[54] HUMAN IMMUNODEFICIENCY VIRUS DECOY

[75] Inventors: Nir Kossovsky; Andrew E. Gelman, both of Los Angeles; Edward E. Sponsler, Burbank, all of Calif.

[73] Assignee: The Regents of the University of California, Oakland, Calif.

[ * ] Notice: The portion of the term of this patent subsequent to Jan. 12, 2010 has been disclaimed.

[21] Appl. No.: 199

[22] Filed: Jan. 4, 1993

Related U.S. Application Data

[63] Continuation-in-part of Ser. No. 690,601, Apr. 24, 1991, Pat. No. 5,178,882, which is a continuation-in-part of Ser. No. 542,255, Jun. 22, 1990, Pat. No. 5,219,577.

[51] Int. Cl.⁵ .................... A61K 9/14; A61K 39/12
[52] U.S. Cl. .................... 424/494; 424/490; 424/493; 424/499; 424/208.1; 514/2; 514/934
[58] Field of Search .............. 424/493, 494, 490, 499, 424/418, 1.1, 3, 4, 88, 89

[56] References Cited

U.S. PATENT DOCUMENTS

| | | | |
|---|---|---|---|
| 4,225,581 | 9/1980 | Kreuter et al. | 424/88 |
| 4,501,726 | 2/1985 | Schröder et al. | 424/1.1 |
| 5,178,882 | 1/1993 | Kossovsky et al. | 424/494 |

OTHER PUBLICATIONS

Kossovsky et al., "Nanocrystalline Epstein-Barr Virus Decoys", Jour. of Appl. Biomaterials, vol. 2, 251-259 (1991).

*Primary Examiner*—Thurman K. Page
*Assistant Examiner*—James M. Spear
*Attorney, Agent, or Firm*—Poms, Smith, Lande & Rose

[57] ABSTRACT

A biologically active composition made up of core particles having diameters of less than about 1000 nanometers which are coated with a layer which is designed to allow attachment of biologically active proteins, peptides or pharmacological agents to the microparticles. When Human Immunodeficiency Virus (HIV) viral protein is attached to the core particles, the result is a viral decoy which accurately mimics native HIV in size, structure and surface character while being entirely devoid of virulent activity due to the microparticle core. The HIV decoy is useful as a vaccine for treating mammals to elicit an immune response.

9 Claims, No Drawings

HUMAN IMMUNODEFICIENCY VIRUS DECOY

BACKGROUND OF THE INVENTION

This is a continuation-in-part of co-pending application Ser. No. 07/690,601 which was filed on Apr. 24, 1991 now U.S. Pat. No. 5,178,882, which is a continuation-in-part of co-pending application Ser. No. 07/542,255 which was filed on Jun. 22, 1990, now U.S. Pat. No. 5,219,577.

FIELD OF THE INVENTION

The present invention relates generally to synthetic biologically active compositions which have a microparticulate core. More particularly, the present invention relates to a synthetic Human Immunodeficiency Virus(HIV) decoy which finds use as a vaccine for Acquired Immune Deficiency Syndrome (AIDS).

DESCRIPTION OF RELATED ART

The attachment of biologically active proteins, peptides or pharmacologic agents to various carrier particles has been an area of intense investigation. These conjugated biological systems offer the promise of reduced toxicity, increased efficacy and lowered cost of biologically active agents. As a result, many different carrier models are presently available. (Varga, J. M., Asato, N., in Goldberg, E. P. (ed.): *Polymers in Biology and Medicine*. New York, Wiley, 2, 73–88 (1983). Ranney, D. F., Huffaker, H. H., in Juliano, R. L. (ed.): *Biological Approaches to the Delivery of Drugs*, Ann. N.Y. Acad. Sci., 507, 104–119 (1987).) Nanocrystalline and micron sized inorganic substrates are the most common carriers and proteins are the most commonly conjugated agents. For example, gold/protein (principally immunoglobulin) conjugates measuring as small as 5 nm have been used in immunological labeling applications in light, transmission electron and scanning electron microscopy as well as immunoblotting. (Faulk, W., Taylor, G., Immunochemistry 8, 1081–1083 (1971). Hainfeld, J. F., Nature 333, 281–282 (1988).)

Silanized iron oxide protein conjugates (again principally antibodies) generally measuring between 500 and 1500 nm have proven useful in various in vitro applications where paramagnetic properties can be used advantageously. (Research Products Catalog, Advanced Magnetics, Inc., Cambridge, Mass., 1988–1989.) Ugelstad and others have produced gamma iron oxides cores coated with a thin polystyrene shell. (Nustad, K., Johansen, L., Schmid, R., Ugelstad, J., Ellengsen, T., Berge, A.: Covalent coupling of proteins to monodisperse particles. Preparation of solid phase second antibody. Agents Actions 1982; 9:207–212 (id. no. 60).) The resulting 4500 nm beads demonstrated both the adsorption capabilities of polystyrene latex beads as well as the relatively novel benefit of paramagnetism.

Carrier systems designed for in vivo applications have been fabricated from both inorganic and organic cores. For example, Davis and Illum developed a 60 nm system comprised of polystyrene cores with the block copolymer poloxamer, polyoxyethylene and polyoxypropylene, outer coats that showed a remarkable ability to bypass rat liver and splenic macrophages. (Davis, S. S., Illum, L., Biomaterials 9, 111–115 (1988)). Drug delivery with these particles has not yet been demonstrated. Ranney and Huffaker described an iron-oxide/albumin/drug system that yielded 350–1600 nm paramagnetic drug carriers. (Ranney, D. F., Huffaker, H. H., In, Juliano, R. L. (ed.): *Biological approaches to the delivery of drums*, Ann. N.Y. Acad. Sci. 507, 104–119 (1987).) Poznasky has developed an enzyme-albumin conjugate system that appears to decrease the sensitivity of the product to biodegradation while masking the apparent antigenicity of the native enzyme. (Poznasky, M. J.: Targeting enzyme albumin conjugates. Examining the magic bullet. In, Juliano, R. L. (ed.): *Biological approaches to the delivery of drugs*, Annals New York Academy Sciences 1987; 507–211:219.)

Shaw and others have prepared and characterized lipoprotein/drug complexes. (Shaw, J. M., Shaw, K. V., Yanovich, S., Iwanik, M., Futch, W. S., Rosowsky, A., Schook, L. B.: Delivery of lipophilic drugs using lipoproteins. In, Juliano, R. L.(ed.): *Biological approaches to the delivery of drugs*, Annals New York Academy Sciences 1987; 507:252–271.) Lipophilic drugs are relatively stable in these carriers and cell interactions do occur although little detail is known.

In any conjugated biological composition, it is important that the conformational integrity and biological activity of the adsorbed proteins or other biological agents be preserved without evoking an untoward immunological response. Spacial orientation and structural configuration are known to play a role in determining the biological activity of many peptides, proteins and pharmacological agents. Changes in the structural configuration of these compounds may result in partial or total loss of biological activity. Changes in configuration may be caused by changing the environment surrounding the biologically active compound or agent. For example, pharmacologic agents which exhibit in vitro activity may not exhibit in vivo activity owing to the loss of the molecular configuration formerly determined in part by the in vitro environment. Further, the size and associated ability of the carrier particle to minimize phagocytic trapping is a primary concern when the composition is to be used in vivo. All of these factors must be taken into account when preparing a carrier particle.

Although numerous different carrier particles have been developed, there is a continuing need to provide carrier particles for both in vivo and in vitro application wherein a biologically active peptide, protein or pharmacological agent can be attached to the particles in a manner which promotes stabilization of the biologically active compound in its active configuration. With respect to in vivo applications, it would be desirable to develop synthetic decoy viruses which could be used as a vaccine to immunize individuals against such dreaded diseases as AIDS.

SUMMARY OF THE INVENTION

In accordance with the present invention, biologically active peptides, proteins or pharmacological agents are attached to a core particle to provide a wide variety of biologically active compositions. The invention is based on the discovery that the surface of ultrafine particles (nanocrystalline particles) can be modified with a surface coating to allow attachment of biologically active moieties to produce compositions wherein the naturally occurring structural environment of the moiety is mimicked sufficiently so that biological activity is preserved. The coating which provides for the attachment of biologically active moieties to nanocrystalline particles in accordance with the present invention can be composed of a basic or modified sugar or oligonucleotide. Coating nanocrystalline particles with a basic sugar or oligonucleotide produces changes in the surface energy and other surface characteristics which make the particles well suited for attachment of biologically active moieties.

In one embodiment of the present invention, nanocrystalline particles are used to prepare a decoy virus wherein the DNA or RNA core of the virus is replaced by the microparticle. The microparticle is chosen to be approximately the same size as the viral core so that the conformation of the surrounding protein coat accurately mimics the native virus. The resulting viral decoy is incapable of infectious behavior while at the same time being fully capable of effecting an immune response and otherwise being antigenically bioreactive.

In this embodiment, an ultrafine particle having a diameter of less than about 1000 nanometers is chosen so as to mimic the DNA or RNA core. Viral peptides attached to the coating surrounding the core have a structure which mimics at least a portion of the native virus. This size of microparticle core is also well suited for carrying anchorage dependent pharmacological agents and other biologically active compounds which require a nanocrystalline particle anchor or core in order to maintain their activity.

As a particular feature of the present invention, a decoy virus is provided which includes viral particles from HIV as at least part of the protein coat. It was discovered that this decoy virus was effective in eliciting cellular and humoral responses in animal models.

The biologically active microparticles in accordance with the present invention have wide-ranging use depending upon the type of biologically active compound which is attached to the microparticle core. When viral protein from HIV is attached to the microparticle core, the result is a decoy virus which may be used as an AIDS vaccine, diagnostic tool or antigenic reagent for raising antibodies. Non-viral protein or antigen coatings may be selected and structured for use in raising specific antibodies or as a diagnostic tool. Further, the microparticles can function as a pharmacological agent when compounds having pharmacological activity are attached to the core particle.

In accordance with the present invention, the utilization of a core microparticle around which HIV viral protein is attached provides an effective way to accurately mimic the antigenic reactivity of native HIV while totally eliminating any of the problems and risks associated with the presence of the viral genetic material. In addition, other proteins, peptides or pharmacological agents may be attached to the core particle to preserve and/or enhance the activity of the compound.

The above-discussed and many other features and attendant advantages of the present invention will become better understood by reference to the following detailed description.

DETAILED DESCRIPTION OF THE INVENTION

The present invention has wide application to immunologic procedures and methods wherein antigenic material or other biologically active moieties are utilized. These areas of application include vaccination agents, antigen agents used to raise antibodies for subsequent diagnostic uses and antigenic compounds used as diagnostic tools. The composition of the invention can also be used in a wide variety of other applications where there is a need to anchor a protein, peptide or pharmacological agent to a core particle in order to preserve and/or enhance bioreactivity.

The compositions of the present invention include nanocrystalline core particles (diameters of less than 1000 nm) which are coated with a surface energy modifying layer that promotes bonding of proteins, peptides or pharmaceutical agents to the particles. The coating modifies the surface energy of the nanocrystalline core particles so that a wide variety of immunogenic proteins, peptides and pharmaceutical agents may be attached to the core particle without significant loss of antigenic activity or denaturization. The result is a biologically active composition which includes a biologically inert core. The end use for the compositions of the present invention will depend upon the particular protein, peptide or pharmacological agent which is attached to the coated core particle. For example, proteins or peptides having antigenic activity may be attached to provide compositions useful as immunodiagnostic tools. Viral fragments or protein coatings having immunogenic activity may be attached to provide a vaccine. Also, pharmacological agents may be attached to provide compositions which are useful in treating diseases.

For preparing decoy viruses for use as vaccines, particles having diameters of between about 10 to 200 nanometers are preferred since particles within this size range more closely mimic the diameter of DNA and RNA cores typically found in viruses.

The core particles may be made from a wide variety of inorganic materials including metals or ceramics. Preferred metals include chromium, rubidium, iron, zinc, selenium, nickel, gold, silver, platinum. Preferred ceramic materials include silicon dioxide, titanium dioxide, aluminum oxide, ruthenium oxide and tin oxide. The core particles may be made from organic materials including carbon (diamond). Preferred polymers include polystyrene, nylon and nitrocellulose. Particles made from tin oxide, titanium dioxide or carbon (diamond) are particularly preferred.

Particles made from the above materials having diameters less than 1000 nanometers are available commercially or they may be produced from progressive nucleation in solution (colloid reaction), or various physical and chemical vapor deposition processes, such as sputter deposition (Hayashi, C., J. Vac. Sci. Technol. A5 (4), Jul/Aug. 1987, pgs. 1375–1384; Hayashi, C., *Physics Today*, Dec. 1987, pgs. 44–60; MRS Bulletin, Jan 1990, pgs. 16–47). Tin oxide having a dispersed (in $H_2O$) aggregate particle size of about 140 nanometers is available commercially from Vacuum Metallurgical Co. (Japan). Other commercially available particles having the desired composition and size range are available from Advanced Refractory Technologies, Inc. (Buffalo, N.Y.).

Plasma-assisted chemical vapor deposition (PACVD) is one of a number of techniques that may be used to prepare suitable microparticles. PACVD functions in relatively high atmospheric pressures (on the order of one torr and greater) and is useful in generating particles having diameters of up to 1000 nanometers. For example, aluminum nitride particles having diameters of less than 1000 nanometer can be synthesized by PACVD using Al $(CH_3)_3$ and $NH_3$ as reactants. The PACVD system typically includes a horizontally mounted quartz tube with associated pumping and gas feed systems. A susceptor is located at the center of the quartz tube and heated using a 60 KHz radio frequency source. The synthesized aluminum nitride particles are collected on the walls of the quartz tube. Nitrogen gas is used as the carrier of the Al $(CH_3)_3$. The ratio of Al $(CH_3)_3$: $NH_3$ in the reaction chamber is controlled by varying the flow rates of the $N_2$/Al$(CH_3)_3$ and $NH_3$ gas into the chamber. A constant pressure in the reaction chamber of 10 torr is generally maintained to provide deposition and formation of the ultrafine nanocrystalline aluminum nitride particles. PACVD may be used to prepare a variety of other suitable nanocrystalline particles.

The core particles are coated with a substance that provides a threshold surface energy to the particle sufficient to cause binding to occur without that binding being so tight as to denature biologically relevant sites. Coating is preferably accomplished by suspending the particles in a solution containing the dispersed surface modifying agent. It is necessary that the coating make the surface of the particle more amenable to protein or peptide attachment. Suitable coating substances in accordance with the present invention include cellobiose, trehalose, isomaltose, maltose, nystose, maltotriose, related basic sugars, and modified sugars such as nitrocellulose. Disaccharides and sugars with relatively high glass transition temperatures are preferred. The glass transition temperature is preferably on the order of about 77° C. Cellobiose is a preferred coating material.

The coating solution into which the core particles are suspended contains, for example, from 1 to 30 weight/volume percent of the coating material. The solute is preferably double distilled water (dd$H_2O$). The amount of core particles suspended within the coating solution will vary depending upon the type of particle and its size. Typically, suspensions containing from 0.1 to 10 weight/volume percent are suitable. Suspensions of approximately 1 weight/volume percent of particles are preferred.

The core particles are maintained in dispersion in the coating solution for a sufficient time to provide uniform coating of the particles. Sonication is the preferred method for maintaining the dispersion. Dispersion times ranging from 30 minutes to a few hours at room temperature are usually sufficient to provide a suitable coating to the particles. The thickness of the coating is preferably less than 5 nanometers. Thicknesses of the coating may vary provided that the final core particles include a uniform coating over substantially all of the particle surface.

The particles are separated from the suspension after coating and may be stored for future use or redispersed in a solution containing the protein or peptide to be attached to the particles. Alternatively, the coated particles may be left in the suspension for further treatment involving attachment of the desired protein or peptide.

The protein or peptide which is applied to the coated particles may be selected from a wide variety of proteins or peptides. Those having antigenic properties are preferred when a vaccine is required. The protein can be the viral protein coat from a selected virus or immunogenic portion thereof. The viral protein coat is isolated according to known separation procedures for isolating and separating viral proteins. The viral coating is the preferred protein because the viral coating is where the antigenic activity of viruses is known to be located. Typically, the virus is digested or solubilized to form a mixture of viral proteins. The viral proteins are then separated by liquid chromatography or other conventional process into the various protein particle fractions and dialyzed to remove impurities.

Suitable viruses from which viral protein particles can be separated and isolated include Epstein-Barr virus, human immunodeficiency virus (HIV), human papilloma virus, herpes simplex virus and pox-virus. Preparations of a wide variety of antigenic protein materials may also be purchased commercially from supply houses such as Microgene Systems, Inc. (400 Frontage Road, West Haven, Conn. 06516), Amgen Corporation (1900 Oak Terrace Lane, Thousand Oaks, Calif. 91320-1789) and Cetus Corporation (1400 53rd Street, Emeryville, Calif. 94608 and Advanced Biotechnology, Inc. (Columbia, Md.). Synthetic peptides and/or proteins which correspond to naturally occurring viral particles may also be utilized.

With respect to HIV, any of the viral fragments which are known to elicit an immune response can be used. Suitable viral fragments include gp120, gp160, gp41, and core proteins (p24). Any of the known techniques for preparing HIV fragments may be used including recombinant methods.

Other biologically active proteins and peptides that can be attached include enzymes, hormones, transport proteins and protective proteins. Human serum transferrin, plasminogen activator and coagulation factors, in addition to the pharmacologic agents amphotericin and insulin, are examples.

The procedure for attaching the antigens or other protein to the coating on the core particles involves suspending the coated core particles in an aqueous solution containing the antigen. The presence in the solution of materials that may preferentially attach to the particle surface is often not advantageous. For example, the dispersion agents present in the solution may create an undesirable coating on the suspended particles prior to protein attachment. Water miscible solvents such as methanol or ethanol may be used. The aqueous solution of coated microparticles can be agitated sufficiently to provide a uniform suspension of the particles. Typically, the amount of particles in solution will be between about 0.5 mg per milliliter of solution and 5 mg per milliliter of solution. Sonication is a preferred method for providing a uniform suspension of the coated particles in solution.

The suspension of coated particles and antigens must be within certain parameters for protein attachment and self assembly to occur. The temperature of the particle solution should be between 1° C. to 45° C. Certain proteins and pharmaceutical agents may be bound to the coated particles in distilled water. Salts may be added to the solution for reactions between coated particles and proteins and other pharmaceutical agents which are unstable or will not disperse readily in distilled water. In general, the salt solutions should be formulated so that the ionic balance (in mM) does not exceed: K=300-500; Na=30-70; Cl=40-150; Ca=0.0003-0.001; and Mg=0.0003-0.001. The oxygen tension of the solution is, advantageously, less than 10% in a solution sparged initially by helium and then gassed with helium, nitrogen and carbon dioxide. The pH of the solution is, advantageously, slightly acidic (relative to blood), with a value, preferably, of between 6.8 to 7.2. An exemplary solution for dispersion of the coated microparticles and for protein attachment is an aqueous solution containing: 0.0360 milligrams MgSo$_4$ per liter, 0.0609 milligrams MgCl$_2$.6H$_2$O, 0.0441 milligram CaCl$_2$.2H$_2$O, 22.823 grams K$_2$HPO$_4$, 13.609 grams KH$_2$PO$_4$, 7.455 grams KCl, and 4.101 gram sodium acetate. The pH of this solution is adjusted to 6.8.

The coated particle cores with the attached protein can be separated from the ionic growth medium and stored for further use. The coated particles may be stored by any of the conventional methods typically used for storing antigenic compounds or antibodies. For example, the coated particles may be freeze dried or stored as a suspension in a compatible solution. When used as a vaccine, the particles coated with a viral protein coat are injected or otherwise administered to the individual according to conventional procedures. Any pharmaceutically acceptable carrier solution or other compound may be used in administering the coated particles to the individual. When used for diagnostic purposes in vitro, the protein coated particles are suspended in solution and used in the same manner as other antigenic compounds. The same is true for use of the protein coated particles for raising antibodies. The same protocol and procedures well known for using antigens to produce antibodies may be used wherein the protein coated particles of the present invention are substituted for normally used antigenic compounds.

The following non-limiting examples describe certain aspects of the present invention in greater detail.

EXAMPLE 1

Preparation of nanocrystalline tin oxide microparticles: 1.5 to 2.0 mg of ultrafine (nanocrystalline) metal powder was placed in a 1.7 ml screw-cap microcentrifuge with 1.5 mls of double distilled water ($ddH_2O$). The $ddH_2O$ was filtered through a rinsed 0.45 micron filter-sterilizing unit or acrodisc (Gelman Scientific). The metal powder was tin oxide with a mean diameter (by photon correlation spectroscopy) of 140 nm. The mixture was vortexed for 30 seconds and placed into a water sonicating bath overnight. The sonication bath temperature was stabilized at 60° C. After a 24-hour sonication, the samples were vortexed once more for 30 seconds with the resulting dispersion clarified by microcentrifugation at approximately 16,000 rpm for 15 seconds. The analysis of particle size was carried out on a Coulter N4MD sub-micron particle analyzer.

The coating was applied to the tin oxide particles by suspending the particles in a stock solution of cellobiose. The cellobiose stock solution was a 292 mM solution made by dissolving 1.000 gram of cellobiose in 9.00 mls of $ddH_2O$. Solution was accomplished at approximately 70° C. in order to promote quick dissolution. The resulting cellobiose solution was filter sterilized through a rinsed 0.45 micron filter with the final volume being adjusted to 10.00 ml.

Sufficient cellobiose stock solution was added to 150 microliters of ultrafine tin oxide dispersion so that the final concentration of the tin oxide was 1.00 percent (w/v) or 29.2 mM. A typical volume for preparation was 2.0 mls which was mixed four or five times by the action of a micro-pipetor. After mixing, the dispersion was allowed to equilibrate for two hours. Demonstration of successful coating of the particles was provided by measuring the mobility of the particles (coated and uncoated) on a Coulter DELSA 440 doppler energy light scatter analyzer. The coated tin oxide particles exhibited a relatively low mobility compared to the non-coated tin oxide particles. Measurements were also taken at various dilute salt concentrations to ensure that the observations with respect to mobility were not artifactual. The tests demonstrate that the particles were coated with the cellobiose.

The coated particles are then used to attach antigenic proteins, peptides or pharmacological agents to prepare bioreactive particles.

EXAMPLE 2

Preparation of nanocrystalline ruthenium oxide particles: The same procedure was carried out in accordance with Example 1, except that ruthenium oxide microparticles were substituted for the tin oxide particles. The ruthenium oxide particles were obtained from Vacuum Metallurgical Company (Japan).

EXAMPLE 3

Preparation of the nanocrystalline silicon dioxide and tin oxide particles: Nanocrystalline silicon dioxide was acquired commercially from Advanced Refractory Technologies, Inc. (Buffalo, N.Y.) and tin oxide was acquired commercially from Vacuum Metallurgical Co. (Japan). The tin oxide particles were also prepared by reactive evaporations of tin in an argon-oxygen mixture and collected on cooled substrates. Nanocrystalline tin oxide was also synthesized by D.C. reactive Magnetron sputtering (inverted cathode). A 3" diameter target of high purity tin was sputtered in a high pressure gas mixture of argon and oxygen. The ultrafine particles formed in the gas phase were collected on copper tubes cooled to 77° K. with flowing liquid nitrogen. All materials were characterized by X-ray diffraction crystallography, transmission electron microscopy, photon correlation spectroscopy, and Doppler electrophoretic light scatter analysis. X-ray diffraction samples were prepared by mounting the powder on a glass slide using double-sized Scotch tape. CuK$\alpha$ radiation was used on a Norelco diffractometer. The spectrum obtained was compared with ASTM standard data of tin oxide. (Powder Diffraction File, Card #21-1250. Joint Committee on Power Diffraction Standards, American Society for Testing and Materials, Philadelphia 1976.) The specimens for (TEM) were collected on a standard 3 mm diameter carbon coated copper mesh by dipping into a dispersion of the (UFP's) in 22-propanol. The samples were examined on a JEOL-STEM 100 CX at an acceleration voltage of 60-80 KV.

To create working dispersions of these metal oxides, 1.5 to 3.0 mg of metal oxide powder was added to 1.5 ml double distilled $H_2O$ in a dust-free screw top microcentrifuge tube (Sarsted) and vortexed for 30 seconds. The mixture was then sonicated for 16 to 24 hours followed by a second 30 seconds vortex. The submicron fraction was then isolated by pelleting macroparticulates by microcentrifugation 16,000 xg for 15 seconds. Approximately 1.3 ml of supernatant was then removed and placed in another dust-free screw top microcentrifuge tube. A sample was prepared for photon correlation spectroscopy (Coulter N4MD) and Doppler electrophoretic light scattering (Coulter delsa 440) analysis by removing 50 to 100 $\mu$l of the dispersion and placing it in a polystyrene cuvette and diluting it to a final volume of 1.00 ml with $ddH_2O$. The stability of the dispersion was determined by sequential measurements over a 24-hour period and was found to be stable. The stability of the dispersion with respect to progressive salinity of the solvent (increasing conductivity) was similarly determined. The stability increased with progressive salinity of the solvent.

1.00 ml of the dispersion was combined and stirred with 8.00 ml of $ddH_2O$ and 1.00 ml of 29.2 mM cellobiose stock in a 15.0 ml capacity ultrafiltration stir cell (Spectra) which has been fitted with a pre-rinsed $5 \times 10^5$ molecular weight cutoff type F membrane (Spectra). The sample was then left to stir for 15 minutes. After stirring, the excess cellobiose was removed by flushing through the cell chamber 250 ml of ddH$_2$O by the action of a peristaltic pump at a rate that does not exceed 10.0 ml/min. After washing, the filtrate was concentrated by the means of pressurized N$_2$ gas to approximately 1.0 ml. Character was established by the removal of 500 ul of the treated dispersion by N4MD analysis. The mean dispersion diameter was re-established at this step. The stability of the coated dispersion was determined by sequential measurements over a 24-hour period. The stability of the coated dispersion with respect to progressive salinity of the solvent (increasing conductivity) was similarly determined.

The resulting coated nanocrystalline particles are suitable for attachment of various proteins, peptides and pharmaceutical agents.

EXAMPLE 4

Preparation, isolation and surface adsorption of human serum transfertin proteins: Nanocrystalline tin oxide was synthesized by D.C. reactive Magnetron sputtering (inverted cathode). A 3" diameter target of high purity tin was sputtered in a high pressure gas mixture of argon and oxygen. The ultra-fine particles formed in the gas phase were collected on copper tubes cooled to 77° K. with flowing liquid nitrogen. All materials were characterized by x-ray diffraction crystallography, selected area electron diffraction, transmission electron microscopy, photon correlation spectroscopy, and energy dispersive x-ray spectroscopy. X-ray diffraction samples were prepared by mounting the powder on a glass slide using double-sized Scotch tape. CuK(alpha) radiation was used on a Norelco diffractometer. The spectrum obtained was compared with ASTM standard data of tin oxide. The specimens for transmission electron microscopy and selected area diffraction were collected on a standard 3 mm diameter carbon coated copper mesh by dipping into a dispersion of the nanocrystalline materials in 2-propanol. The samples were examined on a JEOL-STEM 100 CX at an acceleration voltage of 60-80 KeV. The 2-propanol suspension of particles was also characterized by photon correlation spectroscopy at 22.5° C., 600 s run time on a Coulter N4MD. Energy dispersive x-ray spectroscopy was performed on a JEOL JSM-T330A scanning electron microscope using Kevex quantex V software.

To create working dispersions of these metal oxides for the synthesis of compositions in accordance with the present invention, 0.5 mg of metal oxide powder was added to 1.0 ml of a 29.2 mM cellobiose-phosphate buffered saline solution in a dust free screw top glass vial and sonicated for 20 minutes at 22.5°-35° C. The submicron fraction was then isolated by pelleting macroparticulates by microcentrifugation at 16,000 xg for 30 seconds. Approximately 900 $\mu$l of supernatant was then removed and placed in a dust free screw top microcentrifuge tube. An aliquot was removed for photon correlation spectroscopy (Coulter N4MD) and Doppler electrophoretic light scattering (Coulter DELSA 440) analysis. Aliquots were also removed for characterizing the stability of the coated dispersion over time and with respect to progressive salinity of the solvent (increasing conductivity).

To adsorb protein to the cellobiose coated metal oxide nanocrystalline cores, the core sample was diluted to 10.0 ml with Ca$^{++}$ and Mg$^{++}$ free phosphate buffered saline (Gibco). Forty (40.0) $\mu$g of purified human serum transfertin (4 $\mu$g/$\mu$l) (Gibco), whose antigenicity was verified by ELISA, was then added to a 10 ml stir cell (Spectra). The sample was then left to stir slowly for 30 minutes, taking great care not to allow foaming. After the addition period, 15 ml of Ca$^{++}$ and Mg$^{++}$ free phosphate buffered saline (Gibco) was then washed through the cell under a 2 psi nitrogen gas pressure head. After washing, the sample was again concentrated to 1.00 ml under N$_2$ and a 500 $\mu$l sample was removed for analysis by photon correlation spectroscopy, Doppler electrophoretic light scatter and transmission electron microscopy as detailed below.

Conformational integrity was assessed by measuring the retained antigenicity of the bound protein. To the sample cell, 50.0 $\mu$l of rabbit polyclonal anti-human transfertin antibody (Dako), whose antigenicity was confirmed by ELISA, was added to the concentrated 1.0 ml reaction product at 37.5° C. with gentle stirring. After a 30 minute incubation period, 15 ml of Ca$^{++}$ and Mg$^{++}$ free phosphate buffered saline (Gibco) was then washed through the cell under a 2 psi nitrogen gas pressure head and the reaction volume was again reduced to 1.0 ml.

A 200 $\mu$l aliquot of blocking agent, 1% w/v bovine serum albumin in divalent free saline, was added followed by a 10 minute equilibration period. The secondary antibody, 30 nm gold conjugated goat anti-rabbit polyclonal IgG (Zymed), was then added and the reaction mixture was allowed to incubate for 30 minutes. A sample was removed, chopped on a transmission electron microscopy grid, and vacuum dried. The mixture was again washed with 15 ml of divalent free saline under a nitrogen pressure head and then fixed with glutaraldehyde. One ml of 3% solid bovine collagen (Collagen Corp.) was then added to the mixtures and the composite was ultracentrifuged at $10^6 \times$g for 30 minutes yielding a pellet that was then routinely processed as a biological specimen for transmission electron microscopy. Ten nm thick sections were viewed on a Zeiss transmission electron microscopy. Control samples were prepared as above without the cellobiose intermediate bonding layer.

Transmission electron micrographs showed that the D.C. magnetron sputtered tin oxide was composed of individual particles measuring 20-25 nm in diameter which aggregated into clusters measuring 80 to 120 nm in diameter. By photon correlation spectroscopy, these same particles when dispersed in distilled water produced agglomerates measuring 154±55 nm. The tin oxide particles were fully crystalline as characterized by electron and x-ray diffraction. Energy dispersive x-ray spectroscopy showed no other elements present as impurities.

By Doppler electrophoretic light scatter analysis, tin oxide exhibited a mean mobility of 2.177±0.215 $\mu$m-cm/V-s in aqueous solutions ranging from 10.8 to 20.3 $\mu$M NaCl. Following cellobiose surface coating in a 1% solution, tin oxide exhibited a mean mobility of 1.544±0.241 $\mu$m-cm/V-s in aqueous solutions ranging from 0.0 to 21.0 $\mu$M NaCl. The oxide agglomerated in salt concentrations of greater than 40.0 $\mu$M and in solutions of increasing cellobiose concentration.

Following transferring binding, the crude tin oxide/cellobiose/protein conjugates measured 350±84 nm by photon correlation spectroscopy and transmission electron microscopy. Vacuum dried dropped samples with low concentration gold antibody measured 35–50 nm. Without the cellobiose bonding layer, vacuum dried sections measured 400 to >1000 nm. Occasional antibody bonding was noted. Following high concentration immunogold labeling and filtering, the thin section cellobiose treated specimens measured 50–100 nm. Positive gold binding was identified in approximately 20% of the appropriately coated samples whereas negative controls (prepared as above but lacking the primary rabbit antibody) exhibited approximately 1% nonspecific binding.

As can be seen from the above examples, the biological activity of protein absorbed to the surface of carbohydrate-treated nanocrystalline metal oxide particles is preserved.

EXAMPLE 5

Preparation and Characterization of Epstein-Barr Virus Decoys:

Nanocrystalline tin oxide particles were synthesized by D.C. reactive Magnetton sputtering as previously described in Example 1.

Elutriated sucrose gradient purified Epstein-Bart virus (EBV) acquired from the B95-8 cell line were purchased from Advanced Biotechnologies, Inc., Columbia Md. Each viral aliquot contained approximately $5.00\times10^{10}$ virus particles/ml suspended in 10 mM TRIS-150 mM NaCl ph 7.5 buffer (approximately 0.94 mg/ml protein). The virions were solubilized 0.75% (v/v) Triton X100 and then ultracentrifuged at 150,000xg for 60 minutes to pellet the DNA core using a modification of the method described by Wells. (Wells A, Koide N, Klein G: Two large virion envelope glycoproteins mediate EBV binding to receptor-positive cells. J Virology 1982; 41:286-297.) Following dialysis, the supernatant EBV extract was characterized by both SDS-PAGE (denatured) [Biorad Mini Gel II, 4-20% gradient gel, 200 V$\times$45 minutes and stained with silver] and size exclusion HPLC (non-denatured) [Waters 620 system with a WISP autoinjector and 720 photodiode array detector, 0.5 ml/minute over a Waters SW300 GFC column using a 100 mM NaCl/20 mM TRIS pH 9.4 gradient mobile phase].

Control (non-EBV) proteins were extracted from aliquots of Lambda phage virus [Pharmacia, Milwaukee Wis.] using the same methods as described above.

Aliquots of the tin oxide powder weighing approximately 1.5 mg were initially suspended in 3.0 ml of 29.2 mM cellobiose solution in a dust free glass vial by liberal vortexing [Vortex Genie, Scientific Industries, Bohemia, N.Y.]. The resultant brownish cloudy suspension was then sonified at 175 W for 10.0 minutes at a frequency of approximately 20 kHz at 25° C.[Branson 2" Cup Horn, Branson Ultrasonics Corp., Danbury Conn.]. The dispersion was clarified by microcentrifugation at 16,000xg for 15 seconds. The remaining pellet was then discarded in favor of the supernatant. Unadsorbed cellobiose was removed by ultrafiltration against 20 mls of 25 mM phosphate reaction buffer (pH 7.40 25 mM $HPO_4^{2-}/H_2PO_4^{1-}$) in a 10 kD nominal molecular weight filtered stir cell [Pharmacia] under a 7.5 psi $N_2$ gas head at 37.5° C. Aliquots of the intermediate product were characterized by photon correlation spectroscopy and, following dialysis as described below, by doppler electrophoretic light scatter analysis.

The process of viral protein adsorption was initiated by the removal of the mild triton surfactant from 250 $\mu$l aliquots of EBV extract by ultrafiltration against 25 mls of phosphate reaction buffer at 4° C. in a 10 kD nominal molecular weight stir cell and then adjusted to a concentration of 1.0 $\mu$g/$\mu$l or approximately 1.0 ml final volume. Then 500 ul of the triton free EBV extract was quickly added to a MD nominal molecular weight stir cell with 2.0 ml of the surface treated tin oxide dispersion prewarmed to 37.5° C. The mixture was then slowly stirred while being incubated at 37.5° C. for 2.0 hours. After incubation the unabsorbed EBV extract was removed by ultrafiltration against 25 mls of phosphate reaction buffer.

Control (non-EBV) decoys fabricated with lambda phage viral protein extracts were synthesized using the same process described above.

Intermediate components, the final assembled decoys, and whole Epstein-Barr virions were characterized by doppler electrophoretic light scatter analysis [DELSA 440, Coulter Electronics Inc., Hialeah, FL] to determine their electrophoretic mobility (surface charge) in a fluid phase. Nine phosphate buffer solutions having at 25° C. pH's ranging between 4.59 and 9.06 and corresponding conductivities ranging between 2.290 and 4,720 mS/cm were prepared. Aliquots of raw tin oxide, surface modified cellobiose covered tin oxide, synthesized EBV decoy, and whole EBV were dialyzed against each of the nine solutions and the mobilities of the particulates in dispersion were then measured at field strengths of 4.0, 5.5, 5.5, and 8.0 mA respectively. The mobility values acquired simultaneously by the 4 angled detectors of the instrument were averaged and the means of 3 measurements per dispersion were recorded.

The synthesized EBV decoys and control decoys were characterized by immunoagglutination photon correlation spectroscopy to determine the antibody reactivity of their surfaces. Positive reactivity was assessed by incubating the EBV decoy for 60 minutes at 37.5° C. with a cocktail of anti-EBV murine monoclonal antibodies (1 ug each of anti-EBV-VCA, anti-EBVEA-R, anti-EBVMA, and anti EBV EA-D) in 15% lactose, 0.9% NaCl, 10 mM HEPES buffer, and 0.2% NaN3 [DuPont, Wilmington, Del.]). Background reactivity was assessed by incubating the EBV decoy with irrelevant murine $IgG_1$. Specificity was assessed by reacting the lambda phage decoy with monoclonal anti-EBV murine antibodies. Agglutination was measured by photon correlation spectroscopy at a 90° angle [N4MD, Coulter].

Antibody affinity intensity was assessed by immunogold transmission electron microscopy using the particulates and antibodies listed above and then adding secondary anti-murine 30 nm gold-labeled antibodies (Faulk W, Taylor G. Immunocolloid method for electron microscopy, Immunochemistry 8:1081-1083, 1971).

Labeling of the EBV decoy (positive reaction) was accomplished by incubating a 20 $\mu$l mixture of murine monoclonals (1 $\mu$g anti-EBV-VCA and 1 $\mu$g anti-EBV EA-R in 15% lactose, 0.9% NaCl, 10 mM HEPES buffer, and 0.2% NaN3 [DuPont]) with a fresh 0.5 ml sample of EBV decoy at 37.5° C. for 30 minutes in a 300 kD nominal molecular weigh stir cell. Unbound antibody was then removed by ultrafiltration against 20 mls of phosphate reaction buffer under a 5.0 psi $N_2$ pressure head. After washing, 50 $\mu$l of goat anti-murine antibody covalently fused to 30 nm gold spheres ($10^6$ particles/ml[Zymed Laboratories, San Francisco, Calif.]) were incubated with 200 $\mu$ls of the labeled particles in a 1M nominal molecular weight stir cell at 37.5° C. for 30 minutes. Unbound secondary antibody was removed by ultrafiltration against 10 mls of phosphate reaction buffer.

Labeling of the EBV decoy (negative reaction) was accomplished by incubating 2.5 μl of murine polyclonal nonspecific IgG1 (1-μg/μl in 15 mM NaCl pH 7.4 [Sigma Chemical Corp., St. Louis, Mo.]) with a fresh 0.5 ml sample of EBV decoy as described above followed by the same washing and gold-labeling steps. Labeling of the lambda phage control decoy (negative reaction) was accomplished by incubating a 20 μl mixture of murine monoclonal anti-EBV antibodies with the lambda phage virus coated decoy using the same procedure detailed above.

Immunolabeled particles were prepared for electron microscopy in two ways. A direct immersion technique where a carbon coated copper viewing grid [Ted Pella Inc., Redding, Calif.] was submersed into sample for approximately 5 seconds and then fixed in 5% glutaraldehyde for 1 minute, was used for all reactions as a fast screening technique. A more involved method adding glutaraldehyde directly to the reaction solution, then pelleting the product at 16,000xg for 5 minutes into 0.5 ml soft agar preparation (0.7% agarose [Sea Kem, Temecula, Calif.] in $H_2O$). Then the resultant agar plugs were embedded in plastic and sectioned into 0.1 μm sheets for viewing.

Analysis of both the positive and negative controls was performed by examining pelleted samples of the labeled reaction products by transmission electron microscopy. The relative intensity of antibody binding was determined by counting the number of tin oxide based particles observed to have bound gold spheres (% positive) and then noting the number of gold spheres bound to a given particle (intensity, number/event).

The ultrafine tin oxide particles measured 20-25 nm in diameter and formed aggregates measuring 80 to 120 nm in diameter by transmission electron microscopy. By photon correlation spectroscopy, these same particles when dispersed in distilled water produced agglomerates measuring 154±55 nm. The tin oxide particles were fully crystalline as characterized by electron and x-ray diffraction. Energy dispersive x-ray spectroscopy showed no other elements present as impurities.

Characterization of the EBV proteins by SDS-PAGE showed two distinct protein bands. The first, existing as a dimer suggesting variable glycosylation, exhibited a molecular weight of approximately 350 kd which is consistent with the predominant envelope glycoprotein of EBV. The second exhibited a molecular weight of approximately 67 kd consistent with serum albumin which apparently adsorbs avidly to the viral surface. HPLC confirmed the presence of two distinct bands that exhibited spectrophotometric absorption maxima at 280 nm consistent with proteins. The predominant peak had a chromatographic retention time of 10.30 minutes and could be suppressed 90% by monoclonal anti VCA. The second and relatively minor peak exhibited a chromatographic retention time of 15.75 minutes similar to bovine serum albumin standards.

The previously described Doppler electrophoretic mobility studies conducted between the pH range of 4.5 to 9.0 demonstrated 3 distinct patterns. First, both the decoy and native EB virus retained virtually identical mobilities of approximately −1.4 μm-cm/V-s throughout the pH range. Second, untreated tin oxide exhibited a mobility of approximately −1.0 μm-cm/V-s at a pH of 4.5 which then rose rapidly to −3.0 μm-cm/V-s at pH values of 5.0 and higher. Third, surface modified tin oxide treated with cellobiose retained a mobility of approximately −1.5 μm-cm/V-s until it increased rapidly to −2.5 um-cm/V-s at a pH of 7.5.

The previously described photon correlation spectroscopy showed that native EBV measured approximately 102±32 nm and the synthesized EBV decoy measured approximately 154±52 nm. Synthesized EBV decoy, when reacted with the monoclonal anti-EBV cocktail, agglutinated to form 1534±394 nm masses. Synthesized EBV decoy, when reacted with nonspecific mouse IgG, only increased slightly in size with agglutination diameters of 230±76 nm. Lambda phage decoy, when reacted with the monoclonal anti-EBV cocktail, only increased slightly in size with agglutination diameters of 170±35 nm.

The previously described transmission electron microscopy of anti-EBV antibody labeled EBV decoy particles revealed a positive gold staining frequency of 23.51%±5.53 with an average staining intensity of 7.41 gold labels per event. Examination of non-specific mouse IgG antibody labeled EBV decoy particles revealed a positive gold staining frequency of 5.53%±2.04 with an average staining intensity of 1.00 gold labels per event. Examination of anti-EBV antibody labeled lambda phage decoy particles revealed a positive gold staining frequency of 7.21%±1.26 with an average staining intensity of 1.06 gold labels per event.

EXAMPLE 6

In Vivo Elicitation of Antibodies By Epstein-Barr Virus Decoy: Four sensitization solutions were prepared and delivered once every other week by intramuscular injection in three 250 μl aliquots to New Zealand rabbits aged approximately 8 weeks. The first four animals received approximately $10^9$ whole EBV virions (approximately 32 μg of gp350 estimated by integration of the spectrophotometric absorption curve at 280 nm against a 25 μg bovine serum albumin standard) dispersed in phosphate reaction buffer per injection. The second four animals received 32 μg per injection of isolated and purified gp350 using the same injection protocol. The third group received EBV viral decoys (Example 5) synthesized from a starting aliquot of 32 μg of gp350 per injection. The last group received cellobiose coated in tin oxide dispersed in phosphate reaction buffer. Injections were free of adjuvant. Whole blood was removed using aseptic techniques via cardiac puncture 2 weeks following each of the three injections and the animals were terminated by cardiac puncture followed by lethal sedation at 6 weeks. Serum was extracted by microcentrifugation at 16 kg of whole blood for 1 minute and then stored frozen at −70° C. pending analysis.

Immunospecific antibody against whole EBV virions (ABI) was assayed by ELISA. Approximately $10^9$ virions/ml in phosphate reaction buffer were diluted 1:10 in coating buffer and then allowed to adsorb overnight at 4° C. in polycarbonate assay plates (Falcon). Rabbit serum affinity for the bound EBV virions was determined by the colorimetric reaction of goat anti-rabbit IgG alkaline phosphatase (Sigma) developed with paranitrophenyl phosphate. The concentration of immunospecific IgG were determined by comparison to a calibration curve using nonspecific rabbit IgG as the adsorbed antigen and by subtracting the baseline values recorded from the wells containing serum from the rabbits stimulated with tin oxide only.

Serum collected from the 4 rabbits sensitized with tin oxide showed no increased anti-EBV activity over preimmune serum at any of the three two week sampling intervals. The remaining 3 groups showed a progressive rise in the concentration of anti-EBV specific IgG over the 6 week period. Animals sensitized with purified EBV proteins alone showed a maximum of approximately 0.05 µg/µl anti-EBV IgG at six weeks. In contrast, animals sensitized with either whole EBV or decoy EBV exhibited a statistically significant four fold greater response with approximately 0.20 µg/ul of anti-EBV IgG at six weeks. The immunospecific responses to decoy EBV and whole EBV were virtually identical.

As is apparent from Examples 5 and 6, the synthesized EBV decoy in accordance with the present invention possesses the same surface charge as native virus, is recognized specifically and avidly by monoclonal antibodies, and evokes immunospecific antibodies with the same effectiveness as whole virus. Using photon correlation spectroscopy, the number of particles that agglutinated in the three reaction conditions were calculated from the measured diameters of the aggregates. These calculations indicate that monoclonal anti-EBV antibodies produce agglutinated masses consisting of an average 988.0 decoy EBV particles. Non-specific mouse IgG antibodies produce agglutinated masses consisting of an average 3.33 decoy EBV particles, while monoclonal anti-EBV antibodies produce agglutinated masses consisting of an average 1.35 decoy control lambda phage particles. These measured results show that the measured agglutination potential of the EBV decoy in accordance with the present invention is almost three orders of magnitude greater than controls. The immunogold transmission electron microscopy shows that the gold labeled antibody staining of anti-EBV labeled EBV decoys is 25 to 30 times greater than controls. The ELISA analysis of the immunospecificity of anti-EBV IgG elicited in the rabbits by the EBV decoy is similar to the response elicited by native virus and is 4 fold greater than the response elicited by isolated purified proteins. Examples 5 and 6 are summarized in Kossovsky, N. et al., Nanocrystalline Epstein-Barr Virus Decoys, Journal of Applied Biomaterial, Vol. 2, 251–259, (1991).

EXAMPLE 7

Preparation of HIV Decoys:

The following procedure was used to adsorb HIV membrane antigens onto diamond nanocrystalline particles to provide HIV decoys.

HIV Workup. 1.0 ml of HIV (TCID 50 titre which varied between $10^{5.75}$ to $10^{7.17}$ as determined by the producer Advanced Biotechnology, Inc.) was dialyzed into PBS by 100 KD ultrafiltration and frozen down to −70° C. until needed. On injection day the viral stock was thawed on ice and diluted to 1:25 in PBS. 100 ul of this preparation was used for injection. 1.0 ml of HIV ($10^{5.75}$ transforming units per ml) [ABI] was added to 0.5 ml of envelope extraction buffer [1.0% of Triton X 100/0.25 mM DTT/10 mM Tris pH 7.4/1.0 mM MgCl] and was allowed to incubate for 1.0 hr at room temp. The extract was then ultracentrifuged at 100 K*g for 2.0 hrs[35 krpm SW50.1 Beckman rotor] at 4.0° C. to remove nucleocapsid. Removal of Triton X and envelope protein enrichment was accomplished by incubation with a 300 ul slurry of polystyrene micro beads [Spectra Gel D2] and subsequent 100 kD ultra filtration into PBS. For a 100 ul injection the extract volume was corrected to a 1.0 ml volume and diluted 1:25 in PBS or to a protein concentration of around 2.5 ug/100ul/injection volume. Protein quantization was conducted by HPLC. HPLC conditions were as follows: Waters GFC SW300/Mobile phase:300mMNaCl, 20 mM phosphates pH 7.4/one major peak with a retention time of around 8.9 minutes at a flow rate of 0.5 ml per min/Integration was done against BSA standards.

Preparation of HIV Decoy. HIVex was adjusted to 1.0 ml volume after being ultrafiltered against pH 7.40 20 mM phosphate buffer and was incubated with 1.0 ml of diamond particles which had been coated with 500 mM cellobiose at 4.0° C. for 24 hours. The diamond particles had an average particle size on the order of 50 nm. After adsorption the decoy dispersion was prepared for injection by 300 kD ultrafiltration against PBS to remove unadsorbed protein and was adjusted to 1.0 ml with PBS and parceled out for ten 100 $\mu l$ injections.

Immunological Activity of HIV Decoy

Rabbits, guinea pigs, and mice were injected with either live virus, protein extract, protein extract mixed with Freund's adjuvant, or the HIV decoy virus. Antibody titres against whole virus were measured by ELISA and characterized by western blotting. Cell mediated reactivity was assessed in the guinea pigs by dermal skin challenge with live virus follows by biopsy.

At physiological pH, the mean electrophoretic mobility and average dispersion diameter (50 nm) of these synthetic carriers closely mimicked that of their infectious counterparts. Vaccination of mouse, guinea pig, and rabbit with the HIV decoy elicited the production of antisera which exhibited specific binding to whole HIV preparation as measured by ELISA. The histological analysis of earprick sites for animal sensitized to decoy virus and whole virus showed similar (qualitative and quantitative) reactions which differed significantly from both Freund's-sensitized animals and purified protein-sensitized animals at 1, 2, 7 and 24 weeks. Binding specificity was confirmed by Western blots.

As shown in the above example, the HIV decoy of the present invention has a number of characteristics which are shared with native whole HIV virus. These characteristics include: size, surface charge, immunorecognition, ability to elicit comparable antibody titers, and the magnitude and character of cellular response. These attributes show that the decoy virus in accordance with the present invention can function effectively as a vaccinating agent.

The entire contents of all references cited hereinabove are hereby incorporated by reference.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A vaccine for use in treating an animal to elicit an immune response against the human immunodeficiency virus, said vaccine comprising:

a decoy virus comprising:

a core particle having a diameter of between about 10 to 200 nanometers, said core particle comprising a metal, ceramic or polymer;

a coating comprising a substance that provides a threshold surface energy to said core particle which is sufficient to bind immunologically active fragments of the human immunodeficiency virus without denaturing said immunologically active fragments, said substance covering at least a part of the surface of said core particle and being selected from the group consisting of cellobiose, trehalose, isomaltose, maltose, nystose, maltotriose and nitrocellulose;

at least one immunologically reactive fragment of the human immunodeficiency virus bound to said coated core particle to form said decoy virus; and a pharmaceutically acceptable carrier for said decoy virus.

2. A method for vaccinating an animal to raise antibodies against the human immunodeficiency virus, said method comprising the step of administering to said animal an amount of the decoy virus according to claim 1 sufficient to elicit an immune response which raises said antibodies to said human immunodeficiency virus.

3. A method for vaccinating an animal according to claim 2 wherein said core particle consists essentially of tin oxide.

4. A method for vaccinating an animal according to claim 2 wherein said core particle consists essentially of diamond.

5. A vaccine according to claim 1 wherein said metal is selected from the group consisting chromium, rubidium, iron, zinc, selenium, nickel, gold, silver and platinum.

6. A vaccine according to claim 1 wherein said ceramic is selected from the group consisting of silicon dioxide, aluminum oxide, ruthenium oxide, carbon and tin oxide.

7. A vaccine according to claim 1 wherein said core particle consists essentially of diamond.

8. A vaccine according to claim 1 wherein said fragments of human immunodeficiency virus are selected from the group of fragments consisting of gp 120, gp 160, and gp 41.

9. A method for vaccinating an animal according to claim 4 wherein said coating consists essentially of cellobiose.

* * * * *